United States Patent [19]

Bebee et al.

[11] Patent Number: 5,434,066
[45] Date of Patent: Jul. 18, 1995

[54] MODULATION OF CRE RECOMBINASE IN THE IN VIVO CLONING OF DNA

[75] Inventors: Robert L. Bebee, Gaithersburg; James L. Hartley, Frederick, both of Md.

[73] Assignee: Life Technologies, Inc., Gaithersburg, Md.

[21] Appl. No.: 214,023

[22] Filed: Mar. 15, 1994

Related U.S. Application Data

[63] Continuation of Ser. No. 862,188, Apr. 2, 1992, abandoned, which is a continuation-in-part of Ser. No. 825,267, Jan. 24, 1992, abandoned.

[51] Int. Cl.$^6$ .................. C12N 15/09; C12N 1/21
[52] U.S. Cl. ..................... 435/172.3; 435/252.3; 435/252.33
[58] Field of Search ............ 435/172.3, 252.3, 252.33, 435/320.1

[56] References Cited

U.S. PATENT DOCUMENTS 4,959,317 9/1990 Sauer ................................ 435/172.3

OTHER PUBLICATIONS

Weaver et al. (1989), Genetics (Wm. C. Brown Publishers, Dubuque, Iowa) pp. 194–203.
Amann et al. (1983), Gene 25: 167–178.
Hamilton, D. et al., *J. Mol. Biol.* 178:481–486 (1984).
Hoess, R. et al., *Proc. Natl. Acad. Sci. (U.S.A.)* 79:3398–3402 (1982).
Abremski, K. et al., *J. Biol. Chem.* 259:1509–1514 (1984).
Abremski, K. et al., *Cell* 32:1301–1311 (1983).
Sternberg, N. et al., *J. Mol. Biol.* 187:197–212 (1986).
Sternberg, N. et al., *Cold Spring Harbor Symp. Quant. Biol.* 45:297–309 (1981).
Hoess, R. H. et al., *Proc. Natl. Acad. Sci. (U.S.A.)* 81:1026–1029 (1984).
Sauer, B. et al., *Gene* 70:331–341 (1988).
Palazzolo, M. J. et al., *Gene* 88:25–36 (1990).
Elledge, S. J. et al., *Proc. Natl. Acad. Sci. (U.S.A.)* 88:1731–1735 (1991).
Stratagene (San Diego, Calif.) publication: "λZAP" gene cloning system.
Sauer, B. et al., *New Biol.* 2:441–449 (1990).
Sauer, B., *Molec. Cell. Biol.* 7:2087–2096 (1987).
Abeles, A., *J. Biol. Chem.* 261:3548–3555 (1986).
Austin, S. et al., *Cell* 60:351–354 (1990).
Abeles, A. et al., *Proc. Natl. Acad. Sci. (U.S.A.)* 88:9011–9015 (1991).
Sauer, B. et al., *Nucl. Acids Res.* 17:147–161 (1989).
Hoess, R. et al., *Cold Spring Harb. Symp. Quant. Biol.* 49:761–768 (1984).
Abremski, K. et al., *J. Biol. Chem.* 261:391–396 (1984).
GIBCO BRL Catalogue and Reference, p. 768 (1992).

*Primary Examiner*—Richard A. Schwartz
*Assistant Examiner*—Philip W. Carter
*Attorney, Agent, or Firm*—Howrey & Simon

[57] ABSTRACT

Methods and recombinant vectors suitable for accomplishing the in vivo alteration of a nucleic acid molecule are disclosed. The invention in particular discloses the use of recombinases such as Cre to accomplish in vivo recombination.

7 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: ESCHERICHIA COLI
        ( B ) STRAIN: DH10B ( x i ) SEQUENCE DESCRIPTION: SEQ ID NO:1:

ATAACTTCGT ATAATGTATG CTATACGAAG TTAT        34

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: ESCHERICHIA COLI
        ( B ) STRAIN: DH10B ( x i ) SEQUENCE DESCRIPTION: SEQ ID NO:2:

ATAACTTCGT ATAGCATACA TTATACGAAG TTAT        34

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: ESCHERICHIA COLI
        ( B ) STRAIN: DH10B ( x i ) SEQUENCE DESCRIPTION: SEQ ID NO:3:

CGAAGAGGTA CTGCAGGGGC GATGAGCTTA AATGC        35

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: ESCHERICHIA COLI
        ( B ) STRAIN: DH10B ( x i ) SEQUENCE DESCRIPTION: SEQ ID NO:4:

GATCCTCTAG ATTATTCGGG GAGTTTCAGC TTTGG        35

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: ESCHERICHIA COLI ( x i ) SEQUENCE DESCRIPTION: SEQ ID NO:5:

CGAAGAGGTA CTGCAGCAAT CATTTACGCG TTAATGGC        38

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (vi) ORIGINAL SOURCE:
    (A) ORGANISM: ESCHERICHIA COLI
    (B) STRAIN: DH10B (xi) SEQUENCE DESCRIPTION: SEQ ID NO:6:

GATCCTCTAG ATAAAGGCAG AGCCGATCCT G    31

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: ESCHERICHIA COLI
        (B) STRAIN: DH10B (xi) SEQUENCE DESCRIPTION: SEQ ID NO:7:

CCATAACTTC GTATAATGTA TGCTATACGA AGTTATGGAA ACAGCTATGA CCATGAT    57

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: ESCHERICHIA COLI
        (B) STRAIN: DH10B (xi) SEQUENCE DESCRIPTION: SEQ ID NO:8:

CCATAACTTC GTATAGCATA CATTATACGA AGTTATGTCA CGACGTTGTA AAACGAC    57

MODULATION OF CRE RECOMBINASE IN THE IN VIVO CLONING OF DNA

CROSS-REFERENCE TO RELATED APPLICATIONS

This application is a continuation application of U.S. Patent application Ser. No. 07/862,188 filed Apr. 2, 1992 now abandoned which is a continuation-in-part of U.S. Patent application Ser. No. 07/825,267 filed Jan. 24, 1992, now abandoned.

FIELD OF THE INVENTION

The invention relates to vectors and methods for modulating the expression of enzyme activities, such as ligases, nucleases, and recombinases, in order to thereby facilitate the in vivo cloning of DNA molecules.

BACKGROUND OF THE INVENTION

The techniques of molecular biology have found extensive use in the cloning and analysis of DNA molecules. The most commonly used methods for cloning a gene sequence involve the in vitro use of site-specific restriction endonucleases, and ligases. In brief, these methods rely upon the capacity of the "restriction endonucleases" to cleave double-stranded DNA in a manner that produces termini whose structure (i.e. 3' overhang, 5' overhang, or blunt end) and sequence are both well defined. Any such DNA molecule can then be joined to a suitably cleaved vector molecule (i.e. a nucleic acid molecule, typically double-stranded DNA, having specialized sequences which permit it to be replicated in a suitable host cell) through the action of a DNA ligase. The gene sequence may then be duplicated indefinitely by propagating the vector in a suitable host. Methods for performing such manipulations are well-known (see, for example, Perbal, B. *A Practical Guide to Molecular Cloning*, John Wiley & Sons, NY, (1984), pp. 208–216; Maniatis, T., et al. (In: *Molecular Cloning, A Laboratory Manual*, Cold Spring Harbor Press, Cold Spring Harbor, NY (1982); Old, R.W. et al., In: *Principles of Gene Manipulation*, 2nd. Ed., University of California Press, Los Angeles, (1981), all herein incorporated by reference).

Depending upon the size and characteristics of the desired target molecule, any one of the three different types of vectors—plasmids, bacteriophage, or cosmids—can be employed (See, generally, Watson, J.D., *In: Molecular Biology of the Gene*, 4th Ed., W.A. Benjamin, Inc., Menlo Park, CA (1987), which reference is incorporated herein by reference).

The use of plasmids in cloning is quite well known (see, for example, Cohen et al., U.S. Pat. No. 4,237,224; Itakura, U.S. Pat. No. 4,356,270; Fraley, R.T. et al., PCT Application WO 84/02919; etc.). In general, the most pronounced deficiency of plasmid vectors is the relatively small amount (up to about 5–10 kb) of DNA which can be cloned into them. In general, the larger the size of the target molecule, the lower the efficiency of plasmid transformation.

Bacteriophage vectors, and particularly vectors engineered from the bacteriophage λ have been extensively used as cloning vehicles (see generally, *The Bacteriophage Lambda*, (Hershey, A.D., ed.), Cold Spring Harbor Press, Cold Spring Harbor, NY (1971), and Lambda II, (Hendrix, R. et al., Eds.), Cold Spring Harbor Press, Cold Spring Harbor, NY, pp. 175–209 (1983), Maniatis, T., et al. (In: *Molecular Cloning. A Laboratory Manual*, Cold Spring Harbor Press, Cold Spring Harbor, NY (1982), all herein incorporated by reference). In general, bacteriophage vectors have the advantage that they can be used to clone gene sequences of up to approximately 23 kb.

Cosmids are vectors which have been specifically designed to facilitate the cloning of large DNA molecules. The essential components of a cosmid vector are (1) a drug-resistance marker; (2) a plasmid origin of replication; (3) one or more unique cloning sites that are recognized by a restriction endonuclease; (4) a cos site of bacteriophage λ. Cosmid cloning methods are described, for example, by Maniatis, T., et al, (In: *Molecular cloning, A Laboratory Manual*, Cold Spring Harbor Press, Cold Spring Harbor, NY (1982)). Cosmids vectors can be used to clone 40–50 kb of target molecule. They are thus highly useful in the cloning and analysis of eukaryotic DNA, and especially mammalian genomes. Despite the ease with which in vitro cloning manipulations are often accomplished, serious impediments often limit their application in specific instances.

In vitro cloning may result in genetic rearrangements, deletions or insertions occurring in the desired gene sequence. It often requires the substantial prior purification of gene fragments. Such purification may be impeded if the desired gene fragment does not amplify at the same rate, or with the same fidelity, as other fragments. These concerns are particularly important with regard to the cloning of large DNA fragments, such as those containing human genes and gene families.

Moreover, the capacity to move target molecules from one vector to another in vitro is often limited by the availability or suitability of restriction sites. For example, in order to complete a desired cloning manipulation, it may be necessary to remove a particular enzyme that was needed in an initial cloning step. Such removal would necessitate a time-consuming purification of the cloning intermediate. Thus, a method for effecting the transfer of a target molecule from one vector to another that would not require such intermediate processing would be desirable. The present invention provides such a method and vector molecules for use therein.

SUMMARY OF THE INVENTION

The invention relates to a method for the in vivo manipulation of a cloned target molecule. The method uses a vector molecule that is capable of expressing an activity that acts on a different nucleic acid molecule in order to facilitate the cloning or manipulation of the target molecule.

In detail, the invention provides a method for accomplishing in vivo alteration of a target molecule in a host cell which comprises the steps:

a) providing to the host cell a first vector, the vector containing (i) a preselected gene and (ii) a replicon, wherein the preselected gene is capable of being expressed in the host cell, and the replicon is sufficient to permit the replication of the vector;

b) providing to the host cell a second vector, the vector containing (i) the target molecule which is to be altered, (ii) a replicon, and (iii) a determinant that has the capacity to inhibit the expression of the preselected gene of the first vector;

c) culturing the host cell under conditions sufficient to permit the expression of the preselected gene, to thereby mediate the desired alteration of the target molecule.; wherein the second vector inhibits the expression, and thereby results in the modulation of the expression of the preselected gene.

The invention also includes a host cell containing a first and a second vector, wherein the first vector contains (i) a preselected gene and (ii) a replicon, wherein the preselected gene is capable of being expressed in the host cell, and the replicon is sufficient to permit the replication of the vector; and wherein the second vector contains (i) a target molecule, and (ii) a replicon, and a determinant that has the capacity to inhibit the expression of the preselected gene of the first vector.

The invention also provides a kit, being specially adapted to contain in close compartmentalization:

a) a first container which contains a first vector which contains a replicon and a preselected gene, the vector being capable of expressing the preselected gene in a host cell;

b) a second container, the container containing a second vector, the vector having a determinant that has the capacity to inhibit the expression of the preselected gene of the first vector, and being specially adapted to facilitate the introduction of a desired target molecule.

In particular, the invention includes the embodiments of the above method and host cell and kit wherein the determinant of the second vector inhibits the expression of the preselected gene of the first vector by expressing a gene present on the second vector, wherein the expressed gene of the second vector effects the excision of the preselected gene from the first vector, and wherein the determinant of the second vector inhibits the expression of the preselected gene of the first vector by comprising an incompatibility determinant sufficient to inhibit the replication of the first vector, and thereby causing the loss of the vector from the host cell.

The invention particularly includes the embodiment wherein the alteration is a recombinational alteration, and wherein the preselected gene is a recombinase gene (especially the ere gene), and the target molecule possesses at least one site recognized by the recombinase (such as loxP).

DESCRIPTION OF THE PREFERRED EMBODIMENTS

The present invention provides a method for achieving the in vivo cloning or manipulation of a target nucleic acid molecule. In a preferred embodiment, the method employs a vector, typically a plasmid, that contains, and is capable of expressing, a preselected gene whose expression product has an enzymatic activity that is desired in order to effect the cloning or manipulation of the target molecule. The vector is present in a cell, designated herein as the "host" cell. Any prokaryotic or eukaryotic cell may be used as the host cell of the present invention. The preferred prokaryotic host cell is *E. Coli*. Yeast and mammalian cells comprise examples of preferred eukaryotic host cells.

The target molecule can be introduced into the host cell by electroporation, transfection, transformation, fusion, or any other suitable means. Once present within the host cell, the target sequence is acted upon by the enzymatic activity that results from the expression of the preselected gene. The vector (or other molecule) that contains the preselected gene is preferably resident in the host cell prior to the introduction of the target molecule. However, this is not a requirement of the invention, and the nucleic acid molecules that contain the target molecule and the preselected gene can be introduced simultaneously, or in any order.

I. The Preselected Gene

The present invention employs a preselected gene that is capable of being expressed in the host cell. The gens is preferably present in a vector, most preferably a plasmid vector, however, it may be introduced as a non-replicating nucleic acid fragment (DNA or RNA) (i.e. it need not be a vector).

The expression of the preselected gene will result in the production of a protein that has the ability to interact with the target molecule to thereby alter the structure or characteristic of the target. For example, the preselected gens may encode a ligase, a restriction endonuclease (such as NotI, NdeI or NcoI), a recombinase, a reverse transcriptase, a methylase, etc. The nucleic acid molecule that contains the preselected gene may be constructed such that it contains and expresses only one such preselected gens, or any combination of such genes (such as two or more different methylases, a recombinase and a reverse transcriptase, etc.).

When the preselected gene is a ligase gens, the present invention can be used to mediate the ligation of linear target sequences into a linearized vector. Such linearized molecules may be introduced into the host cell via transformation, electropotation, etc. Thus, such preselected genes are desirable in facilitating the cloning of target fragments.

When the preselected gene is a restriction enzyme gens, the present invention can be used to mediate the sitespecific, in vivo cleavage of the target molecule. Thus, such preselected genes are desirable in facilitating the purification or sub-cloning of target fragments.

When the preselected gene is a methylase gene, the present invention can mediate the site-specific, in vivo modification of the target molecule so as to render it resistant to restriction endonuclease cleavage. Thus, such preselected genes are desirable in facilitating the cloning of intact target molecules.

When the preselected gene is a reverse transcriptase gene, the present invention can be used to accomplish the cDNA cloning of any mRNA species present in the host cell.

In a preferred embodiment the preselected gene will be a recombinase gene. The product expressed by such a gene —a "recombinase" —is an enzymatic activity that is capable of recombining two nucleic acid molecules. Thus, such preselected genes can be used to mediate the transfer of a linear target molecule into a vector molecule, or the transfer of the target molecule from one vector to another. Significantly, such transfer is not dependent upon the presence of restriction sites at the termini of the target sequence. Likewise, such transfer is not precluded by the presence of restriction sites within the target sequence. All that is required is that the target sequence be flanked by sites recognized by the recombinase. Where the target molecule is a linear molecule, such sites may be naturally present at the termini, but more commonly will be added to the target sequence via ligation or primer extension. Where the target sequence is a circular molecule, such sites can be introduced into molecule via restriction enzymes, homologous recombination, or site-specific recombination.

Two classes of recombinases are known. A "general recombinase" is an enzymatic activity that is capable of participating in a process which results in the scission of two nucleic acid molecules having identical or substantially similar sequences (i.e. "homologous"), and the ligation of the two molecules such that one region of each initially present molecule becomes ligated to a region of the other initially present molecule (Sedivy, J.M., Bio-Technol. 6:1192–1196 (1988), which reference is incorporated herein by reference). The most characterized general recombination system is that of the bacteria E. coli (Watson, J.D., In: Molecular Biology of the Gene, 4th Ed., W.A. Benjamin, Inc., Menlo Park, CA (1987); Smith, G.R., In: Lambda II, (Hendrix, R. et al., Eds.), Cold Spring Harbor Press, Cold Spring Harbor, NY, pp. 175–209 (1983)). The E. coli system involves the protein, RecA, which in the presence of ATP or another energy source, can catalyze the pairing of DNA molecules at regions of homology.

In the most preferred embodiment of the present invention, the preselected gene will encode a "site-specific recombinase." In contrast to a general recombinase, "site-specific recombinase" can recognize only certain defined sequences as substrates for recombination. The more preferred of the site-specific recombinases are the Int, Int/Xis, and Cre recombinases. The Cre recombinase of bacteriophage P1 is the most preferred site-specific recombinase. The Cre recombinase of P1 is discussed by Sternberg, N. et al. (J. Molec. Biol. 187:197–212 (1986)), herein incorporated by reference.

The term "Cre" recombinase, as used herein, refers to a protein having an activity that is substantially similar to the site-specific recombinase activity of the Cre protein of bacteriophage P1 (Hamilton, D.L., et al., J. Mol. Biol. 178:481–486 (1984), herein incorporated by reference). The Cre protein of bacteriophage P1 mediates site-specific recombination between specialized sequences, known as "loxP" sequences:

(SEQ ID NO:1) 5' ATAACTTCGTATAATG-TATGCTATACGAAGTTAT 3'
(SEQ ID NO:2) 5' ATAACTTCGTATAG-CATACATTATACGAAGTTAT 3'

The loxP site has been shown to consist of a double-stranded 34 bp sequence (SEQ ID NOS: 1 and 2). This sequence contains two 13 bp inverted repeat sequences which are separated from one another by an 8 bp spacer region (Hoess, R., et al., Proc. Natl. Acad. Sci. (U.S.A.) 79:3398–3402 (1982); Sauer, B.L., U.S. Pat. No. 4,959,317, herein incorporated by reference).

ere has been purified to homogeneity, and its reaction with the loxp site has been extensively characterized (Abremski, K., et al., J. Mol. Biol. 259:1509–1514 (1984), herein incorporated by reference). Cre protein has a molecular weight of 35,000. Cre protein can be obtained commercially from New England Nuclear/Du Pont. The cre gene (which encodes the Cre protein) has been cloned and expressed (Abremski, K., et al., Cell 32:1301–1311 (1983), herein incorporated by reference).

The Cre protein mediates recombination between two loxP sequences (Sternberg, N., et al., Cold Spring Harbor Symp. Quant. Biol. 45:297–309 (1981)). These sequences may be present on the same DNA molecule, or they may be present on different molecules. Because the internal spacer sequence of the loxP site is asymmetrical, two loxP sites can exhibit directionality relative to one another (Hoess, R.H., et al., Proc. Natl. Acad, Sci. (U.S.A.) 81:1026–1029 (1984)). Thus, when two sites on the same DNA molecule are in a directly repeated orientation, Cre will excise the DNA between the sites (Abremski, K., et al., Cell 32:1301–1311 (1983)). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites.

Two circular molecules each having a single loxP site will recombine to form a mixture of monomer, dimer, trimer, etc. circles. Higher concentrations of circles favor higher n-mers; lower concentrations of circles favor monomers.

A circular DNA molecule having a single loxP site will recombine with a linear loxp-containing DNA molecule to produce a larger linear molecule. The converse reaction of a linear molecule with direct repeats of loxP sites is thus the production of a circle containing the sequences between the loxP sites, and remaining linear. However, if the loxP sites are inverted repeats, recombination flips the sequence between the loxP sites back and forth. Thus, the interaction of loxP and Cre can cause either circularization of a linear molecule or the linearization of an appropriate circularized molecule.

In one embodiment, the Cre protein may be the expression product of a mutated cre gene, and may interact with mutated loxP sites. Suitable mutations have been produced both in Cre, and in the loxP site. The Cre mutants thus far identified have been found to catalyze recombination at a much slower rate than that of the wild-type Cre protein. loxP mutants (such as loxP511) have been identified which recombine at lower efficiency than the wild-type site (Abremski, K., et al., J. Biol, chem, 261:391–396 (1986); Abremski, K., et al., J. Mol. Biol. 202:59–66 (1988), herein incorporated by reference).

It has been found that certain E. coli enzymes inhibit efficient circularization of linear molecules which contain two loxP sites. Hence, enhanced circularization efficiency can be obtained through the use of E. coli mutants which lack exonuclease V activity (Sauer, B., et al., Gene 70:331–341 (1988)).

Cre has been able to mediate loxp specific recombination in Saccharomyces cerevisiae (Sauer, B., Molec. Cell. Biol. 7:2087–2096 (1987); Sauer. B.L., U.S. Pat. No. 4,959,317, herein incorporated by reference), and in mammalian cells (Sauer, B., et al., Proc. Natl. Acad. Sci. (U.S.A.) 85.:5166–5170 (1988), Sauer, B., et al., Nucleic Acids Res. 17:147–161 (1989), both references herein incorporated by reference). Similarly, the recombination system has been capable of catalyzing recombination in plant cells (Dale, E.C., et al., Gene 91:79–85 (1990)).

A large number of alternative suitable site-specific recombinase have been described, and their genes can be used in accordance with the method of the present invention. Such recombinases include the Int recombinase of bacteriophage λ (with or without Xis) (Weisberg, R. et. al., In: Lambda II, (Hendrix, R. et al., Eds.), Cold Spring Harbor Press, Cold Spring Harbor, NY, pp. 211–250 (1983), herein incorporated by reference), TpnI and the β-lactamase transposons (Levesque, R.C., J. Bacteriol. 172:3745–3757 (1990)); the Tn3 resolvase (Flanagan, P.M et. al., J. Molec. Biol. 206:295–304 (1989); Stark, W.M. et al., Cell 58:779–790 (1989)); the yeast recombinases (Matsuzaki, H. et al., J. Bacteriol. 172:610–618 (1990)); the B. subtilis SpoIVC recombinase (Sato, T. et al., J. Bacteriol. 172:1092–1098 (1990)); the Flp recombinase (Schwartz, C.J. et al., J. Molec.

Biol. 205:647–658 (1989); Parsons, R.L. et al., J. Biol. Chem. 265:4527–4533 (1990); Golic, K.G. et al., Cell 59:499–509 (1989); Amin, A.A. et al., J. Molec. Biol. 214:55-72 (1990)); the Hin recombinase (Glasgow, A.C. et al., J. Biol. Chem. 264:10072–10082 (1989)); immunoglobulin recombinases (Malynn, B.A. et al., Cell 54:453-460 (1988)); and the Cin recombinase (Hafter, P. et al., EMBO J. 7:3991–3996 (1988); Hubnet, P. et al., J. Molec. Biol. 205:493-500 (1989)), all herein incorporated by reference.

Such systems are discussed by Echols, H. (J. Biol. Chem. 265:14697-14700 (1990)), de Viiiarray, J.P. (Nature 335:170–174 (1988); Craig, N.L. (Ann. Rev. Genet. 22:77–105 (1988)), Poyart-Salmeron, C. et al. (EMBO J. 8:2425-2433 (1989)), Hunger-Bertling, K. et al. (Molec. Cell, Biochem. 92:107-116 (1990)), and Cregg, J.M. (Molec. Gen. Genet. 219:320-323 (1989)), all herein incorporated by reference.

Cre is the preferred recombinase of the present invention because its site-specific recombinase activity is dependent only upon the presence of the loxP site and Cre. No energy is needed for this reaction; thus, there is no requirement for ATP or other similar high energy molecules. Moreover, no factors or proteins other than the Cre protein is required in order to mediate sites specific recombination at loxP sites (Abremski, K., et al., J. Mol. Biol. Chem. 259:1509-1514 (1984); Hoess, R.P., et al., Cold Spring Harbor Symp. Qant. Biol. 49:761-768 (1984), herein incorporated by reference).

The use of plasmids having direct repeats of loxP sites to mediate gene cloning is discussed by Palazzolo, M.J. et al. (Gene 88:25-36 (1990)), and Elledge, S.J. et al. (Proc. Natl. Acad, Sci., (U,S,A.) 88:1731-1735 (1991)). Site-specific cleavage (but without a recombinase) is used in the "λZAP" gene cloning system of Stratagene (San Diego, CA).

II. The Modulation of the Expression of the Preselected Gene

Because many preselected genes encode proteins whose activities, like that of the Cre protein, are capable of catalyzing forward and reverse reactions (under normal host cell culturing conditions), it is desirable to be able to modulate the expression of the preselected gene, such that after a period sufficient to permit the expression of the gene has transpired, further expression will be limited, or will not occur.

A nucleic acid molecule that encodes a recombinase, such as ere, may be used to recombine a target molecule having loxP sites into a suitable loxP site-containing vector. Similarly, it may be employed to remove a target molecule from such a vector.

A. Reversible Modulation

In one embodiment of the present invention, the nucleic acid molecule that contains the preselected gene is constructed such that the expression of the preselected gene can be reversibly modulated. As used herein, the term "reversibly modulated" is intended to denote that the expression of the gene can be repeatedly turned on and off. Such modulation may be qualitative (i.e. in which the preselected gene is either fully expressed, or fully repressed) or quantitative (in which intermediate levels of expression are possible). Most preferably, this embodiment is achieved through the use of nucleic acid molecules that are vectors, and hence capable of autonomous replication within the host cell.

Suitable modulation can be obtained by expressing the preselected gene using inducible/de-repressible promoters and their respective inducers/de-repressors (for example, plac with IPTG, ptrp with IAA, λ pL with a λ temperature sensitive cI repressor, precA (or λ pL with a normal λ cI repressor) with UV light or mitomycin C, etc.).

Alternatively, the preselected gene can be mutated such that its product is conditionally active. Examples of such mutations include temperature sensitive mutations and "amber" mutations (when the host cell has a temperature sensitive amber suppressor), etc.

Where the preselected gene is naturally expressed on a bacteriophage, it is possible to employ the bacteriophage directly. Thus, for example, Cre can be provided to cells by infecting them with bacteriophage P1, the natural source of Cre. Desirably, a P1 mutant (such as a P1 which is deficient in replication, lysis, maturation, etc.) is employed to prevent cell death.

B. Irreversible Modulation

In a preferred embodiment, the vector is constructed such that modulation of the preselected gene is irreversible. As used herein, the term "irreversible modulation" is intended to denote that once the expression of the gene has been turned off, it cannot be re-expressed. Thus, cessation of the expression of the preselected gene is permanent, and irreversible.

Such irreversible modulation is desirable when the preselected gene is a restriction endonuclease gene or a ligase. Irreversible modulation is particularly desirable in those cases wherein the preselected gene is capable of not only converting the target molecule into a desired reaction product, but also converting the produced reaction product back into the original target molecule. Such modulation is therefore especially desirable in the case of a preselected gene that encodes a recombinase such as Cre.

Irreversible modulation can be achieved in any of a variety of ways. The preselected gene can be introduced into a host cell as a non-vector molecule. Such a molecule may, for example, be a linear or circular molecule, a molecule lacking an origin of replication, or a molecule that does not possess an origin of replication that is recognized by the replicative apparatus of the host cell, or a molecule that is not properly partitioned upon cell division. When such a molecule is introduced into the host cell, its preselected gene will be expressed. However, due to the inability of the cell to replicate the preselected gene, such expression will be transient, and will ultimately cease as the cell divides and loses the nucleic acid molecule that contains the preselected gene. Since such molecules are incApable of replication, they are ultimately degraded by nucleases or other cellular processes.

In another embodiment, irreversible modulation is achieved through the use of vectors (carrying the preselected gene) that are conditionally incApable of replication or partition in the host cell. Such vectors may contain, for example, temperature sensitive replicons or temperature sensitive partition proteins (such as parA or ParB of P1, sopA or sopB of P1, etc.). In this embodiment, the host cell is incubated in the presence of the target molecule and the vector under a replication permissive temperature. After the desired expression of the preselected gene has occurred, the temperature is adjusted to a non-permissive temperature such that additional replication of the vector is impaired.

In another embodiment, the vector that contains the preselected gene may additionally contain and express a "negative" selectable marker gene, such that the expression of the marker gene imparts a conditionally selectable disadvantage to the host cell. In this embodiment, the host cell is incubated in the presence of the target molecule and the vector under permissive conditions. After the desired expression of the preselected gene has occurred, the culturing conditions are adjusted such that continued maintenance of the vector is selected against.

In a more preferred embodiment, the host cell will be constructed such that it contains a "determinant" that has the capacity to inhibit the expression of the preselected gene. As used herein, a "determinant" can be either a site or regulatory element, or an expressible gene. The determinant may be present on the nucleic acid molecule that contains the target molecule, on the nucleic acid molecule that contains the preselected gene, or on any other nucleic acid molecule (including the cell's chromosome)).

For example, the preselected gene may be present in the vector in combination with recombinogenic or cleavable sites, such that the expression of the preselected gene results in the excision of the gene from the vector, and the ultimate loss of the gene from the cell. Most preferably, the preselected gene and the recombinogenic sites will be selected such that the excision reaction is irreversible. This can be accomplished, for example by using the λint gene (encoding the Int recombinase) as the preselected gene, and flanking this gene with an attP and attB site. Expression of Int will lead to the excision of the λint gene from the vector, and the conversion of the attP and attB sites into attL and attR sites. Since Int is effectively incApable of mediating recombination at attL and attR sites (in the absence of the λ Xis protein), it is unable to catalyze the reinsertion of the λint gene into the vector. Thus, the initial expression of the λint gene results in an irreversible modulation of its expression.

In a similar manner, vectors containing other preselected genes, such as the Cre gene, can be employed. For example, the host cell can be constructed to contain and express the λint gene (the gene may be present on the target molecule, the nucleic acid molecule that contains the preselected gene, or any other nucleic acid molecule (including the cell's chromosome)), and the desired preselected gene (for example, cre) can be present on a nucleic acid molecule flanked by the attP and attB sites, as described above. In lieu of the λint gene, other recombinases (such as mutant Cre proteins) or other recombinogenic sites such as loxP511 can be employed.

Most preferably, irreversible modulation of the expression of the preselected gene will be accomplished through the use of vector molecules having incompatible replicons or incompatible partition requirements (Abeles, A., J. Biol. Chem. 261:3548–3555 (1986); Austin, S. et al., Cell 60:351–354 (1990); Abeles, A. et al., Proc. Natl. Acad. Sci. (U.S.A.) 88:9011-9015 (1991), all herein incorporated by reference).

Preferably, incompatibility is mediated using the P1 replicon (which controls P1 copy number in cells). The P1 replicon consists of an origin sequence (P1 ori), an essential replication protein (RepA) and dispensable regulatory elements known as incA and incC. Naturally, the incA element contains 9 copies of a DNA sequence motif that binds RepA protein. Hence, by increasing the number of RepA binding sites present in a cell, it is possible to attenuate or inhibit the replication of P1 or any vector that is replicated using the P1 replicon (Abeles, A., J. Biol. Chem. 261:3548–3555 (1986)).

Accordingly, the preselected gene is introduced into the host cell on a vector that has a P1 ori, and a repA gene. The vector may additionally contain one or more incA and/or incC sites. More preferably, it will lack at least one, and most preferably all, of the incA sites naturally associated with the P1 replicon. The absence of the incA sites serves to enhance the copy number of the vector (to about 10 copies per cell).

In this embodiment, the target molecule is adapted to contain an incompatibility determinant comprising part or all of the incA element (preferably comprising at least two, and more preferably three RepA binding sites), such that the introduction of the target molecule into a host cell (containing the P1 ori vector) will prevent the vector from replicating. Preferably, the target molecule will be present in a suitable cloning site of a vector. Desirably, this vector will have a replicon that results in a high copy number per cell. The pUC replicon (Yanisch-Perron, C. et al., Gene 33:103 (1985)) is preferred for this purpose.

Cre protein (or nucleic acid encoding the Cre protein) can also be provided to cells via the introduction of capsules, liposomes, empty bacteriophage particles, etc. Such introduction can be accomplished by electroporation, micro-injection, infection, etc.

The present invention includes articles of manufacture, such as "kits." Such kits will, typically, be specially adapted to contain in close compartmentalization a first container which contains a first vector which contains, and is capable of expressing a preselected gene, especially, the cre recombinase. The first vector will additionally contain a replicon (preferably a P1 replicon), such that the replication of the first vector can be inhibited or prevented by the presence of an incompatibility determinant. The incompatibility determinant is contained on a second vector molecule present in a second container of said kit. The second vector molecule is adapted (as by possessing restriction endonuclease cleavable cloning sites) to receive a desired target nucleic acid molecule. Preferably, the first vector molecule will lack at least one, and preferably all of the incA associated RepA binding sites naturally present in the P1 replicon, and will therefore have an enhanced copy number (of about 10 copies per cell). Preferably, the second vector molecule will be a high copy number plasmid (most preferably a plasmid having a pUC replicon). The kit may additionally contain instructional brochures, and the like. It may also contain reagents sufficient to accomplish DNA cloning (such as restriction endonucleases, ligases, buffers and the like).

Having now generally described the invention, the same will be more readily understood through reference to the following examples which are provided by way of illustration, and are not intended to be limiting of the present invention, unless specified.

EXAMPLE 1

CONSTRUCTION OF A PREFERRED CRE EXPRESSION PLASMID: pZIP

A preferred Cre expression plasmid was made by ligating together 3 PCR products each of which contained a separate function. The three fragments are (1) the P1 ori, (2) the cre gene, and (3) a kanamycin resistance determinant, Kan$^R$ gene. The sources of these fragments were as follows. Added restriction sites are underlined. All P1 replicon coordinates are taken from Abeles, A. (J. Biol. Chem. 261:3548-3555 (1986)); all cre gene coordinates are taken from Sternberg, N. et al. (J. Molec. Biol. 187:197-212 (1986)), both herein incorporated by reference.

P1 ori:

To obtain a fragment that contains the P1 ori, PCR amplification of the P1 origin was performed. For such amplification, a left and right primer pair was used. The left primer was about 70 bp upstream of start of P1 ori (coordinate 291-309) and has a PstI site in its 5'-end (oligo#923)(SEQ ID NO:3):
5' CGAAGAGGTACTGCAGGGGCGAT-GAGCTTAAATGC 3'

The right primer was at very end of repA gene (coordinate 1501-1524) and has XbaI in 5'-end (oligo#924)(SEQ ID NO:4):
924: 5' GATCCTCTAGATTATTCGG-GGAGTTTCAGCTTTGG 3'

The primers were used with P1 vir phage as target, and the PCR yielded a 1261 bp product.

Cre gene:

The cre gene of the vector was obtained through PCR using a set of a left and a right primer pair. The right primer corresponded to coordinate 1465-1484 +PstI site (oligo#793)(SEQ ID NO:5):
793: 5' CGAAGAGGTACTGCAGCAAT-CATTTACGCGTTAATGGC 3'

The left primer corresponded to coordinate 380-399 (oligo#925)+XbaI site (SEQ ID NO:6): #925: 5' GATCCTCTAGATAAAGGCAGAGC-CGATCCTG 3'

The amplification yielded an 1134 bp product, that included a single cre promoter.

The primers were used against a P1/λ (P1/lambda) hybrid phage (Sternberg, N., J. Molec. Biol. 150:603-609 (1981)).

Kan$^R$ gene:

In order to obtain the kanamycin resistance determinant, oligonucleotides which flank the multiple cloning site of pUC4K (Pharmacia) were used to give a PCR product of about 1400 bp with flanking PstI sites. The PstI sites are not in the primers—they are in the amplified sequence in the multiple cloning site (MCS). The primers that were used for this amplification are #790 (SEQ ID NO:7):
5' CCATAACTTCGTATAATGTATGCTATAC-GAAGTTATGGAAACAGCTATGACCAT-GAT 3'
and #791 (SEQ ID NO:8):
5' CCATAACTTCGTATAGCATACATTATAC-GAAGTTATGTCACGACGTTGTAAAAC-GAC 3' After PCR, reactions were digested with the following restriction endonucleases:
P1 ori fragment: PstI and XbaI,
cre gene : PstI and XbaI, and
kan$^R$ gene : PstI. The resulting fragments were gel purified, mixed, and ligated. The resulting product was transformed into E. coli DH10B then selected for resistance to kanamycin (Kan$^R$). The cre gene-containing plasmid was designated pZIP. Colonies harboring "pZIP" showed Cre activity by in vitro assay of crude cell sonicates.

EXAMPLE 2

CONSTRUCTION OF A PREFERRED VECTOR FOR CONTAINING THE TARGET MOLECULE:
λZipLox

Vectors derived from bacteriophage λ often are used for the construction of cDNA libraries, especially when target clones will be identified by immunological screening procedures (Huynh, T.V., In DNA Cloning: A Practical Approach (Vol. 1) (D. M. Glover, ed.) IRL Press Limited, Oxford, England, p. 49 (1985)). However, once a clone is identified, the next step is usually to subclone the cDNA into a plasmid vector to facilitate propagation, characterization, and manipulation of the DNA.

The use of the methods of the present invention permit the automatic in vivo subcloning of DNA molecules from λ vectors by exploiting the highly site-specific Cre-loxP recombinational machinery of bacteriophage P1. λZipLox is the term used to designate the preferred vector for containing the target molecule.

λZipLox is prepared by incorporating a plasmid, designated pZL, into a lambda phage. In the presence of Cre, the pZL plasmid is excised from the vector.

Plasmid pZL is a 4.3 kb derivative of GIBCO BRL plasmid pSPORT1. Plasmid pZL was prepared by first using PCR to amplify that part of the incA region of the P1 regulon that containing repeats 1, 2, and 3. The PCR was performed against a P1 vir phage target using oligos #937 and #938 (coordinates 1939-1960 and 2043-2068, respectively, as designated in Genbank record PP1REP, Genbank release 63.0) as primers:
(SEQ ID NO: 9)
937: 5' GCGGCCAACATGGTGG-GCACACATATTTGATACCAGCGA 3'
(SEQ ID NO: 10)
938: 5' GGCCAAGATCTTGGACTGGT-GAGAACGGCTTGCCCGGCAG 3'

This incA fragment was then cloned into the BspHI site (coord. 3569) of vector pSPORT1 (Life Technologies, Gaithersburg, MD) to make the construct pSAX10. When this region was sequenced, three mutations were found which varied from the published sequence of incA: A instead of C at coordinate 1736, C instead of T at coordinate 1784, and A instead of G at coordinate 1819.

Next, a loxP site was cloned into the other BspHI site of the plasmid (coordinate 2561). This was accomplished by PCR amplifying the Kanamycin resistance gene of plasmid pUC4K (Pharmacia) with primers #790 and #791. The resulting product contained the kan$^R$ gene flanked by directly repeated lox sites. All other features of pSPORT1 are fully preserved in pZL.

This product was ligated to pSAX10 that had been cut with BspHI at coordinate 2561 and the ends made blunt. Kanamycin-resistant clones were then selected.

When the resulting plasmid was treated with Cre in vitro and transformed into E. coli cells, clones which had become Kanamycin sensitive were detected. One of these was shown to have a functional loxP site and was designated pZL.

λZipLox was constructed from ligation of a 23.1 kb HindIII fragment derived from the left arm λgt10 a 12.7 kb SalI fragment derived from the right arm of a deletion mutant of λgtll [the 260 bp XhoI (position 33500) to SalI (position 33240) fragment removed; lambda coordinates are from Lambda II (Hendrix, R.W. et al., Eds.), Cold Spring Harbor Laboratory, Cold Spring Harbor, New York (1983)) and pZL linearized by Cre-mediated recombination with i oligonucleotides to yield HindIII and SalI compatible termini.

λZipLox is approximately 40.1 kb long, with a predicted size limit for cDNA inserts of 10.1 kb based on a theoretical capacity of 50.2 kb. Following the conventions of Sambrook et. al. (Sambrook, J. et al., In: *Molecular Cloning: A Laboratory Manual*, 2nd Ed., Cold Spring Harbor Laboratory, Cold Spring Harbor, New York (1989)), the genotype of λZipLox is λsrIλ1° shndIIIλ1° <loxP pMB1 ori lacI lacZ' T7 promoter-multiple cloning site-SP6 promoter lacZ' incA amp loxP) ssIIλ1° sxIλ1° cits857 srIλ4° nin5 srIλ5° Sam100. A simplified representation of λZipLox is "left arm of bacteriophage lambda—loxP site—plasmid pZL—loxP site—right arm of bacteriophage lambda".

λZipLox contains seven unique restriction sites for cloning cDNA within the multiple cloning site (EcoRI, SalI, SstI, SpeI, NotI, XbaI and SplI). DNA inserts cloned into the multiple cloning site of λZipLox reside within the inducible lacZ' gene commonly found in pUC-type plasmid vectors. When the lac promoter is induced with IPTG, the cloned gene is expressed as a fusion protein embedded within the amino-terminal portion of the β-galactosidase fragment encoded by lacZ'. Thus, λZipLox can be used to detect antigens expressed from cloned genes in the same manner as the popular λgt11-based systems.

The λZipLox system solves the troublesome problem associated with the Cre-mediated recombination-dependent automatic subcloning vector described by Palazzolo, M.J., et al. (*Gene* 88:25 (1990)). They reported reduced yields of plasmids containing a LoxP site in cells expressing the Cre recombinase constitutively. The λZipLox system eliminates this problem by incorporating a biological switch into the λZipLox system that automatically reduces the level of Cre recombinase after PZL is excised from λZipLox: it uses the incompatibility between plasmids containing the P1 origin of replication and the P1 incA locus to mediate the elimination of the cre-producing plasmid from the cell.

Immediately upon entering the cell, plasmid PZL (and any DNA cloned into it) is excised and circularized from the λZipLox genome by Cre-loxP recombination. This process also yields an intact λ phage, however, by simply using a lambda lysogen as the host cell, the expression of the λ phage can be repressed (by the resident λ prophage). The preferred host for this purpose is a strain DH10BZIP. DH10BZIP is a derivative of *E. coli* DH10B that was made by lysogenization of DH10B (F-mcrA Δ(mrr−hsdRMS-mcrBC) φ80dlacZΔM15 ΔlacX74 endA1 recA1 deoR Δ(ara,-leu)7697 araD139 galU galK nupG rpsL) with λNIH W82 (λxis6 ind-), followed by transformation with pZIP. DH10BZIP expresses Cre recombinase constitutively, and is thus preferred for the automatic excision of PZL plasmids from clones isolated from λZipLox libraries. The introduction of λZipLox (or any vector containing incA sites) will irreversibly modulate Cre expression.

EXAMPLE 3

LAMBDA ZIPLOX PROTOCOL

A. Ligation of CDNA to Lambda Ziplox

| | | |
|---|---|---|
| Lambda Ziplox NotI-SalI arms | 0.5 μg | 0.5 μg |
| CDNA NotI-SalI ends | 50 ng | — |
| 5X T4 DNA Ligase Buffer | 1 μl | 1 μl |
| T4 DNA Ligase (1 unit/μl) | 1 μl | 1 μl |
| autoclaved distilled water | to 5 μl | to 5 μl |

1. Prepare two ligation mixes in two 1.5 ml autoclaved microcentrifuge tubes. One ligation mix does not have CDNA and will be the background.
2. Mix by pipetting up and down with pipettor. Minifuge briefly to collect contents at the bottom of the tube.
3. Incubate the ligation mixes at room temperature for 3 to 4 hours. Alternatively, the ligations can proceed overnight at 16° C.

B. Packaging of the Ligation Mix

1. Use Lambda Packaging Mix (Life Technologies, Inc., Gaithersburg, MD, USA; cat. 8294SA), or equivalent, according to manufacture's directions.
2. Remove one blue tube (Extract A, Y00123, Life Technologies, Inc.) and one yellow tube (Extract B, Y01141, Life Technologies, Inc.) for each packaging reaction to be performed. Extract A is prepared from *E. coli* BHB2688 (lambda E−(am))); Extract B is prepared from *E. coli* BHB2690 (lambda D−(am))), see, Hohn, B. et al., *Proc. Natl. ACad. Sci.* (U.S.A.) 74:3259 (1977). Place both tubes immediately on ice. One packaging reaction should be the Control Lambda that comes with the packaging kit. It will serve as a control to see if the packaging works. Use 2 μl (0.5 μg) of the Control Lambda.
3. Thaw the extracts on ice. The contents should be collected at the bottom of the tube by briefly minifuging.
4. Transfer the entire ligation mix (5 μl) to the blue tube as soon as the extracts have thawed.
5. Immediately transfer 15 μl from the yellow tube into the blue tube and mix gently by stirring with the pipette tip and gently pipetting up and down. Do not vortex. Collect the contents at the bottom of the tube by briefly minifuging.
6. Incubate at room temperature for 2 hours.
7. Add 0.5 ml phage dilution buffer to the tube. Add 20 μl of chloroform to the tube. Mix gently. Let chloroform settle for 10 minutes, or minifuge for 1 minute. Store packaged phage at 4° C.

C. Plating of Packaged Lambda

1. Grow up 5 ml of the appropriate strain (Y1090R−) in TYN containing 10 mM Mg, 0.2% maltose, 0.1 mg/ml ampicillin at 37° C. Use 0.5 A590/ml as the concentration of cells to use to plate. They can be diluted in phage dilution buffer.
2. Mix 100 μl of the diluted packaged phage with 200 μl of the diluted cells (Y1090R−) in a sterile 13×100 glass tube or a sterile Falcon 2059 tube. Incubate at 37° C. for 15-20 minutes.
3. Add 3 ml molten (50° C.) TYN top agar containing 10 mM Mg, 0.1 mg/ml ampicillin, and pour onto 100×15 mm TYN plates.

4. When top agar is set (5 minutes), invert the plates and incubate overnight at 37° C.
5. The background packaged mix should be diluted to 1:100 for plating. The Lambda Ziplox with cDNA insert should be diluted to 1:100, 1:1000, and 1:10,000. The control Lambda should be diluted to 1:100,000 and 1:1,000,000.

D. Excision

1. Grow DH10BZIP in TYN, 10 mM Mg, 0.2% maltose, 10 μg/ml kanamycin at 37° C.
2. Transfer a plaque from the plate to a sterile 1.5 ml microcentrifuge tube containing 250 μl of phage dilution buffer.
   a. With a scalpel or razor blade, cut about 5 mm off of a sterile pipette tip, so that the opening approximates the size of the plaque to be transferred.
   b. Place the shortened tip onto a P200 Pipetman and carefully aspirate the plaque into the tip.
   c. Transfer the plaque into the phage dilution buffer by pipetting up and down.
3. Incubate at room temperature 1–2 hours.
4. Mix 10 μl of the supernatant from the soaked plaque with 100 μl of DH10BZIP cells in a sterile Falcon 2059 tube, and incubate at room temperature for 15–20 minutes.
5. Add 400 μl SOC to each tube, and incubate shaking at 37° C. for 60 minutes.
6. Plate 5–20 μl onto a TYN plate containing 0.01% X-gal, 2 mM IPTG, and 0.1 mg/ml ampicillin. This can be done by diluting the 5–20 μl into 100 μl of SOC before spreading onto the plate.
7. Invert the plates and incubate them at 37° C. overnight.

The following reagents are used:

A. Phage Dilution Buffer (50 mMTris buffer pH 7.9, 100 mM NaCl, 10 mMMgCl, 0.01% gelatin. This solution should be made up from sterile stocks and sterile water, or it should be made up and then autoclaved.

B. TYN media (10 gm Tryptone, 5 gm Yeast extract, 5 gm NaCl, 10 ml 1 M Tris buffer pH 7.2, 225 μl 10 N NaOH, water to 1 liter). Autoclave, then add the following different reagents depending on what type of media is required:
   a. 10 mMMg
      Add 100 μl of 1M MgCl per 10 ml of media.
   b. 0.1 mg/ml ampicillin
      Add 100 μl of 10 mg/ml ampicillin per 10 μl of media.
   c. 10 μg/ml kanamycin
      Add 10 μl of 10 mg/ml kanamycin to 10 ml of media.
   d. 0.2% maltose
      Add 100 μl of 20% maltose to 10 ml of media.

C. TYN plates (10 gm Tryptone, 5 gm Yeast extract, 5 gm NaCl, 10 ml 1M Tris buffer pH 7.2, 225 μl 10 N NaOH, 17–20 gm agar. Autoclave, and cool to about 60° C. before adding other reagents. Then pour about 20 ml into sterile petri dishes. Let set before storing them at 4° C. The following are different reagents that could be added depending on what type of plates are required.
   a. 10 mMMg
      Add 10 ml of sterile 1M MgCl to 1 liter of TYN.
   b. 0.1 mg/ml ampicillin
      Add 10 ml of sterile 10 mg/ml ampicillin to 1 liter of TYN.
   c. 0.01% X-gal
      Add 2.5 ml of 4% X-gal to 1 liter of TYN.
   d. 2 mM IPTG
      Add 20 ml of 100 mM IPTG to 1 liter of TYN.

D. 0.7% Top Agar (or agarose) (100 ml TYN media, and 0.7 gm agar (or agarose). Autoclave. If using immediately, place in a 60° C. water bath to keep from solidifying. If it solidifies, re-melt it in a microwave oven. Be sure to loosen cap. Agarose is sometimes used instead of agar if plaque lifts are desired. There is less chance of the agarose sticking to the filters. If desired, the following may be added to the top agar:
   a. 10 mMMg
      Add 10 μl of 1M MgCl per ml of top agar.
   b. 0.1 mg/ml ampicillin
      Add 10 μl of 10 mg/ml ampicillin per ml of top agar.

E. 10 mg/ml ampicillin. Prepared by weighing out 5 gm of ampicillin and adding it to 500 ml of distilled water. Mix until in solution. Sterile filter the solution and store at 4° C.

F. 1 M MgCl$_2$. Prepared by weighing out 20.33 gm of MgCl$_2$.6H$_2$O, and adding it to 100 ml of distilled water. Mix until in solution. Sterile filter or autoclave the solution.

G. 20% Maltose. Prepared by weighing out 20 gm of maltose and add it to enough distilled water to come to a final volume of 100 ml. Mix until in solution. Autoclave the solution.

H. 4% X-gal
1. Mix 1 gm of X-gal with enough dimethylformamide to come to a final volume of 25 ml. Store at −20° C.

I. 100 mM IPTG. Prepared by mixing 1 gm of IPTG with enough sterile distilled water to come to a final volume of 41 ml. Store at −20° C. Wrap container in foil to keep light out.

J. 10 mg/ml kanamycin. Prepared by mixing 0.5 gm of kanamycin with enough sterile distilled water to come to a final volume of 50 ml. Store at 4° C. Wrap container in foil to keep light out.

In the above described examples, the following materials were obtained from Life Technologies, Inc.: T4 DNA Ligase and 5X T4 DNA Ligase Buffer (5224SB); Lambda Packaging System (8294SA); S.O.C. Medium (5544SA); X-gal (5520UC); and IPTG (5529UA).

EXAMPLE 4

CONSTRUCTION OF A CDNA LIBRARY IN λZIPLOX AND EXPRESSION SCREENING

In order to verify the utility of the λZipLox system, a HeLa cDNA library was constructed in λZipLox that had been digested with Not I and Sal I.

*E. Coli* Y1090R−[ΔlaCU169 proA+hadR−hsdM+− Δlon araD139 strA supF[trpC22::Tn10]pMC9 (pMC9=pBr322-lacI$^Q$)] was cured of the resident plasmid, and the resulting strain used to plate and screen the HeLa cDNA library. By screening the induced library with primary antibody to human vimentin, followed by reaction with alkaline phosphatase-conjugated secondary antibody, four vimentin-positive clones were recovered from approximately 10$^5$ plaques. The plasmids from these were excised in vivO, and the 3'-terminal regions of the inserts sequenced. The sequences of the four clones were identical to each other (except for the length of the poly A tail derived from the vimenticmRNA) over the 100 bp sequenced. However, the sequence differed at six positions from the published sequence for the 3' terminal region of human vimentin cDNA (Ferrari, S. et al., *Molec. Cell Biol.* 6:3614 (1986)).

The excision process described here has several clear advantages over other automatic subcloning techniques. The excision efficiency (i.e., the conversion of input phage particles to colonies) is about 50%. Moreover, unlike M13-based systems, the λZipLox system does not require infection with helper phage, and so is more rapid. Selection for the desired excised recombinant is as simple as infecting the host cell with the λZipLox clone of interest, and then selecting for $Ap^R$ bacterial colonies. Additionally, the vector does not pass through a single-stranded intermediate that requires packaging into a phage particle, processes that may cause deletions in cloned inserts (Michel, B. et al., *Proc. Natl. Acad. Sci.* (U.S.A.) 84:3386 (1986)).

When plasmid DNA is prepared from clones after excision, the distribution of plasmid between monomer and dimer forms varies. This has practical consequences for those who prefer to screen clones for plasmid insert size by examining supercoiled DNA rather than linearizing or excising the cloned fragment to estimate its size. For the HeLa library, midscreen preparations from 17 randomly-chosen clones showed that two yielded predominantly monomer, while seven yielded predominantly dimer. The remaining clones yielded an approximately equal amount of each form of DNA. This may be a function of the effective level of Cre recombinase at the time of infection, or an indirect effect of the insert itself. The Cre recombinase gene may be placed on a low copy-number replicon to achieve the lowest level of Cre expression consistent with efficient excision.

EXAMPLE 5

INCOMPATIBILITY BETWEEN pZL AND pZIP

In order to assess the effects of incompatibility between pZL and pZIP, plasmids pSPORT (containing neither loxP sites nor incA elements), pSPORTLoxP (containing a loxP site but no incA element), and pZL (containing, as described above, both loxP sites and incA elements), were introduced into the pZIP-containing *E. coli* strain DH10BZIP. 100 μl of cells and 1 μl of plasmid were used for each reaction. After the transformation, the cells were plated on LB medium supplemented with ampicillin (100 μg/ml) and methicillin (200 μg/ml). Five transformants of each plasmid were selected and cultured in SB medium supplemented with ampicillin (100 μg/ml) and grown overnight.

Mini-preps were performed to assess yields of the pSPORT-derived plasmids in DH10BZIP. 1 ml of the overnight culture was centrifuged, and plasmid was extracted. The preparation was dissolved in 100 μl T(1/10)E buffer with RNase. 5 μl of each preparation was then digested with ScaI in RE6 buffer, and the restriction pattern was analyzed via electrophoresis (37° C. 30 minutes, 0.9% H-58).

The cells of the five colonies of pSPORT / pZip control transformants were all found to contain both of these plasmids. The cells of the five colonies of pSPORTloxP / pZip control transformants were also found to contain both plasmids, however, the yield of pSPORTLoxP was much lower (estimated 5-10 fold) than pSPORT. The continued presence of the pZIP plasmid in these cells indicates that, as expected, Cre expression had not been modulated.

In contrast, the cells of the five colonies of pZL / pZip transformants were all found to contain only the pZL plasmid; the presence of the incA locus on the pZL plasmid had successfully eliminated the pZIP plasmid. Moreover, a substantial increase in pZL concentration was observed; the yield of pZIP being higher than the yield of pSPORT.

These data indicate that the presence of Cre in the cells (from the pZIP plasmid) had no effect on replication of pSPORT (because pSPORT has no loxP site), but severely inhibited replication of pSPORTLoxP (presumably by binding to the loxP site and preventing passage of the replication complex around the circular molecule (see, Palazzolo, M.J., et al. (*Gene* 88:25 (1990)). Incompatibility of pZL with pZip resulted in rapid loss of pZip, and thus rapid loss of Cre protein, allowing normal replication. However, many of the pZL molecules were present as dimers or higher multimers, which may account for the higher yield of pZL than of pSPORT.

Three transformant colonies of each of the above transformations were diluted $10^3$-fold in LB and then plated on medium containing either ampicillin/methicillin or kanamycin. The ability of cells to grow in the presence of ampicillin/methicillin indicates the presence of either pSPORT, pSPORT! oXP, or pZL. The ability of cells to grow in the presence of kanamycin indicates the presence of pZIP. The results of this experiment are shown in Table 1.

TABLE 1

| TRANSFORMANT | COLONIES PER PLATE | | SUMMARY DATA |
|---|---|---|---|
| | AMP | KAN | |
| pSPORT 1 | 913 | 1054 | $\Sigma_{amp} = 1,093$ |
| pSPORT 2 | 108 | 107 | $\Sigma_{kan} = 1,226$ |
| PSPORT 3 | 72 | 65 | |
| pSPORTLoxP 1 | 289 | 306 | $\Sigma_{amp} = 1,495$ |
| pSPORTLoxP 2 | 871 | 936 | $\Sigma_{kan} = 1,565$ |
| pSPORTLoxP 3 | 335 | 323 | |
| pZL 1 | 185 | 0 | $\Sigma_{amp} = 922$ |
| pZL 2 | 307 | 0 | $\Sigma_{kan} = 0$ |
| pZL 3 | 430 | 0 | |

AS shown in Table 1, all of the pZL transformants were found to have lost the pZIP plasmid. When pZL /pZIP transformants were grown on medium containing both ampicillin and kanamycin no colonies formed, indicating that dual selection could not "force" the maintenance of the pZIP plasmid in the presence of pZL.

The experiment shown in Table 1 was repeated, except that for the pZL / pZIP transformants, 1, 10, and 100 μl of the undiluted stock of cells were plated. This permitted a determination of whether the transformants contained any kanamycin resistant cells. The results of this experiment are shown in Table 2.

TABLE 2

| TRANSFORMANT | COLONIES PER PLATE | | SUMMARY DATA |
|---|---|---|---|
| | AMP | KAN | |
| pSPORT 1 | 140 | 138 | $\Sigma_{amp} = 544$ |
| pSPORT 2 | 183 | 191 | $\Sigma_{kan} = 496$ |
| pSPORT 3 | 221 | 167 | |
| pSPORTLoxP 1 | 222 | 207 | $\Sigma_{amp} = 414$ |
| pSPORTLoxP 2 | 61 | 64 | $\Sigma_{kan} = 411$ |
| pSPORTLoxP 3 | 131 | 140 | |
| pZL 1 | 98 | 0 | $\Sigma_{amp} = 979$ |
| pZL 2 | 167 | 0 | $\Sigma_{kan} = 0$ |
| pZL 3 | 714 | 0 | |

After adjustment for the dilution factor, the results indicated that the pSPORT transformants contained 1.8×10⁶ amp^R cells / colony, and 1.65×10⁶ kan^R cells / colony. Thus, the results indicate that all cells of the colony contain both pSPORT and pZIP. The results also indicated that the pSPORTloxR transformants contained 1.38×10⁶ amp^R cells / colony, and 1.37×10⁶ kan^R cells / colony. Thus, the results indicate that all cells of these colonies contain both pSPORTLoxP and pZIP.

In contrast, although the pZL transformants contained 3.26×10⁶ amp^R cells / colony, no kan^R cells were obtained. Thus, the pZL transformant colonies contained less than 10 kan^R cells / colony (i.e. less than 1 kan^R cell per 3×10⁵ amp^R cells). The results indicate that the presence of the pZL plasmid led to the loss of the pZIP plasmid from the host cell.

In order to further demonstrate the utility of the present invention, the Cre-expressing host cell DH10BZIP was infected with λZipLox. After permitting phage adsorption, the cells were plated on medium containing ampicillin (100 μg/ml) and methicillin (200 μg/ml) and allowed to form colonies. The number of colonies which formed was approximately half that of the number of λZipLox phages forming plaques, indicating that Cre-mediated excision had occurred after infection in approximately 50% of input λZipLox. Colonies of ampicillin/methicillin resistant cells were diluted and plated on either medium containing ampicillin or medium containing kanamycin, in the manner described above. The ampicillin resistant colonies contained less than 1 kan^R cell per 2×10⁶ amp^R cells. The results indicate that the presence of the pZL plasmid led to the efficient excision of the pZIP plasmid from λZipLox, and that the presence of the incA elements on pZL successfully rendered the host cell incompatible to pZIP, and caused the loss of the pZIP plasmid.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

What is claimed is:

1. A method for accomplishing in vivo site-specific recombination between Lox sites of a target molecule in a host cell which comprises the steps:
    (A) providing to said host cell a first vector, said vector containing (i) a Cre recombinase gene and (ii) a replicon, wherein said Cre recombinase gone is capable of being expressed in said host cell and said replicon is sufficient to permit repliCatiOn of said first vector:
    (B) providing tO said host cell a second vector, said second vector containing (i) said target molecule and lox sites, (ii) a replicon, and (iii) a determinant that has the capacity tO inhibit the expression of siad Cre recombinase oene of said first vector: wherein said inhibition is irreversible and;
    (C) culturing said host cell under conditions sufficient to permit the expression of said Cre recombinase gone, to thereby mediate the in vivo site-specific recombination of the lox sites of said second vector, said site-specific recombination causing the excision of said target molecule from said second vector; wherein said second vector inhibits expression of said Cre recombinase, and, thereby results in the modulation of the expression of said Cre recombinase gene.

2. The method of claim 1, wherein said determinant of said second vector inhibits the expression of said Cre recombinase gens on the first vector by expressing a gens present on said second vector.

3. The method of claim 1, wherein said determinant of said second vector comprises an incompatibility determinant sufficient to inhibit the replication of said first vector and cause the loss of said first vector from the said host cell.

4. The method of claim 3, wherein said replicon of said first vector is a P1 replicon that lacks at least one naturally present incA regulatory element, and wherein said second vector contains an incA regulatory element, such that the presence of said second vector inhibits the replication of said first vector.

5. A host cell containing a first and second vector, wherein said first vector contains (i) a Cre recombinase gene and (ii) a replicon wherein said Cre recombinase gens is capable of being expressed in said host cell and said replicon is sufficient to permit replication of said first vector; and wherein said second vector contains (i) a target moleCUle containing lox sites recognized by said Cre recombinase gene, (ii) a replicon, and (iii) a determinant that has the capacity to inhibit the expression of said Cre recombinase gene of said first vector wherein said determinant of said second vector comprises an incompatibility determinant sufficient to inhibit the replication of said first vector.

6. The host cell of claim 5, wherein said replicon of said first vector is a P1 replicon, and wherein said incompatibility determinant comprises an incA regulatory element.

7. The host cell of claim 6, wherein said P1 replicon of said first vector lacks at least one naturally present incA regulatory element.

* * * * *